Figure 1:
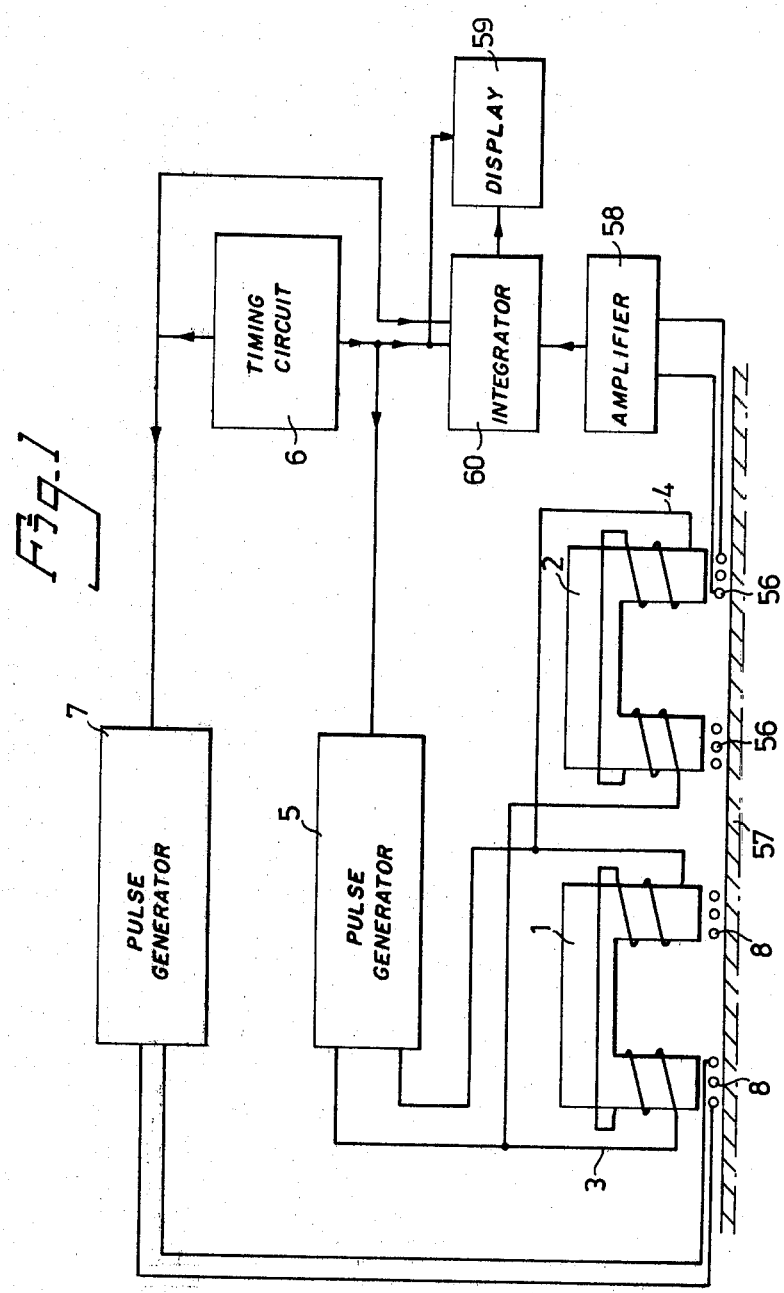

United States Patent [19]

Spijkerman

[11] 4,314,479
[45] Feb. 9, 1982

[54] METHOD AND APPARATUS FOR TRANSMITTING AND RECEIVING ELECTROMAGNETICALLY GENERATED AND RECEIVED ULTRASONIC PULSES

[75] Inventor: Johan Spijkerman, Nyköping, Sweden

[73] Assignee: Studsvik Energiteknik AB, Nyköping, Sweden

[21] Appl. No.: 89,983

[22] Filed: Oct. 31, 1979

[30] Foreign Application Priority Data

Nov. 7, 1978 [SE] Sweden ............................ 7811513

[51] Int. Cl.³ ............................................ G01N 29/04
[52] U.S. Cl. ................................................... 73/643
[58] Field of Search ........................ 73/643, 627, 632

[56] References Cited
U.S. PATENT DOCUMENTS 4,164,873 8/1979 Böttcher et al. ..................... 73/643

Primary Examiner—Anthony V. Ciarlante
Attorney, Agent, or Firm—LeBlanc, Nolan, Shur & Nies

[57] ABSTRACT

A method and an apparatus for transmitting and receiving electromagnetic ultra-sound, especially in nondestructive testing of electrically conductive material, comprising the steps of generating one or more magnetic fields by means of one or more electromagnets (1,2,3,4) and supplying a transmitter coil (8) in said magnetic field with a supersonic frequency, and scanning a receiver coil (56) in said magnetic field. In known apparatuses, especially in the testing of non-magnetic material, the signal/noise ratio of a received signal is unfavorable.

According to the present invention said ratio is improved in that said magnetic field is generated during a short time compared with the time between two successively occurring magnetic fields, and that a number of pulses of well-defined length of supersonic frequency are supplied to the transmitter coil (8) when the magnetic field or fields have a sufficient strength.

The receiver coil (56) is scanned after each such pulse, and the different receiver signals are summed up in an integrator (60). The said pulses each have a preferred length of a complete sinusoidally-shaped cycle, whereafter the respective pulse is extinguished entirely.

12 Claims, 4 Drawing Figures

METHOD AND APPARATUS FOR TRANSMITTING AND RECEIVING ELECTROMAGNETICALLY GENERATED AND RECEIVED ULTRASONIC PULSES

This invention relates to a method and an apparatus for transmitting and receiving electromagnetically generated and received ultrasonic pulses.

The invention particularly relates to a method, which is especially advantageous in the non-destructive testing of non-magnetic material, and to an apparatus for the same purpose.

In electromagnetic ultrasonic tests ultra-sound is introduced non-contactingly into a body of electrically conductive material by means of a strong magnetic field, where a coil in the field is fed with a current of supersonic frequency. The receiver includes a receiving coil in a strong magnetic field, in which coil a signal is generated when the body vibrates with supersonic frequency in the magnetic field of the receiver.

This principle, thus, is well-known. One example of its utilization is defect indication in steel or other electrically conductive material.

The signal strength, however, received in the receiver is low in relation to the noise level occurring when this technique is used for testing non-magnetic material. For this reason, the technique heretofore has been applied substantially only to the testing of magnetic material where the signal/noise ratio is much more favourable.

The present invention has the object to increase the signal/noise ratio to such a degree, that the technique advantageously can be applied to the non-destructive testing of non-magnetic electrically conductive material. One very important example of utilizing the present invention is the detection of defects in steel workpieces or products in a state heated above the Curie-temperature.

By the method and apparatus according to the invention the signal/noise ratio is improved radically in the testing of both non-magnetic and magnetic material. The present invention relates to a method of transmitting and receiving electromagnetically generated pulses of ultra-sound, especially in the non-destructive testing of electrically conductive material, comprising the steps of generating one or more magnetic fields by means of one more electromagnets and supplying a transmitter coil in said magnetic field with a signal of supersonic frequency, and of scanning a receiver coil in said magnetic field. The method is characterized in that said magnetic field is generated by a first pulse generator during a time which is short as compared with the time between two successively occurring magnetic fields, that after the magnetic field or fields have assumed the desired strength, preferably 50 percent of maximum strength, a series of pulses well-defined in length of supersonic frequency are generated by means of a second pulse generator and are supplied to said transmitter coil, that the receiver coil after each such pulse is scanned with respect to a signal corresponding to said pulse, that every such signal is stored in an integrator such that the series of received signals corresponding to said series of pulses are summed up, whereafter the signal summed up in the integrator is caused to be emitted to a unit for illustrating or processing the signal, and that the last pulse in said series is emitted when said magnetic field has decreased to a desired strength, preferably 50 percent of maximum strength.

The invention further relates to an apparatus for transmitting and receiving electromagnetically generated pulses of ultrasound, especially in the non-destructive testing of electrically conductive material, comprising one or more electromagnets for generating one or more magnetic fields, a transmitter coil and a receiver coil located at the poles each of its own or of the same electromagnet, and means for supplying said electromagnets and transmitter coil with energy. The apparatus is characterized in that said last mentioned means comprise a first pulse generator capable of supplying energy to the electromagnet or -magnets in the form of a pulse during a short time as compared with the time between two successive pulses, and a second pulse generator capable to generate a series of pulses well-defined in length of supersonic frequency, which second pulse generator is capable of generating and supplying the pulses to the transmitter coil when the magnetic field or fields have assumed desired strength, preferably 50 percent of maximum strength, until the magnetic field or fields have decreased to corresponding desired strength, that scanning means are provided to scan the receiver coil with respect to a received signal corresponding to every said pulse in said series, which scanning means comprise an integrator capable of digitally storing the series of received signals corresponding to said series of pulses and of summing up the signals thus received, and capable after each such series of pulses of emitting the summed up signal to a unit for illustrating or processing the summed up signal.

Figure 2:
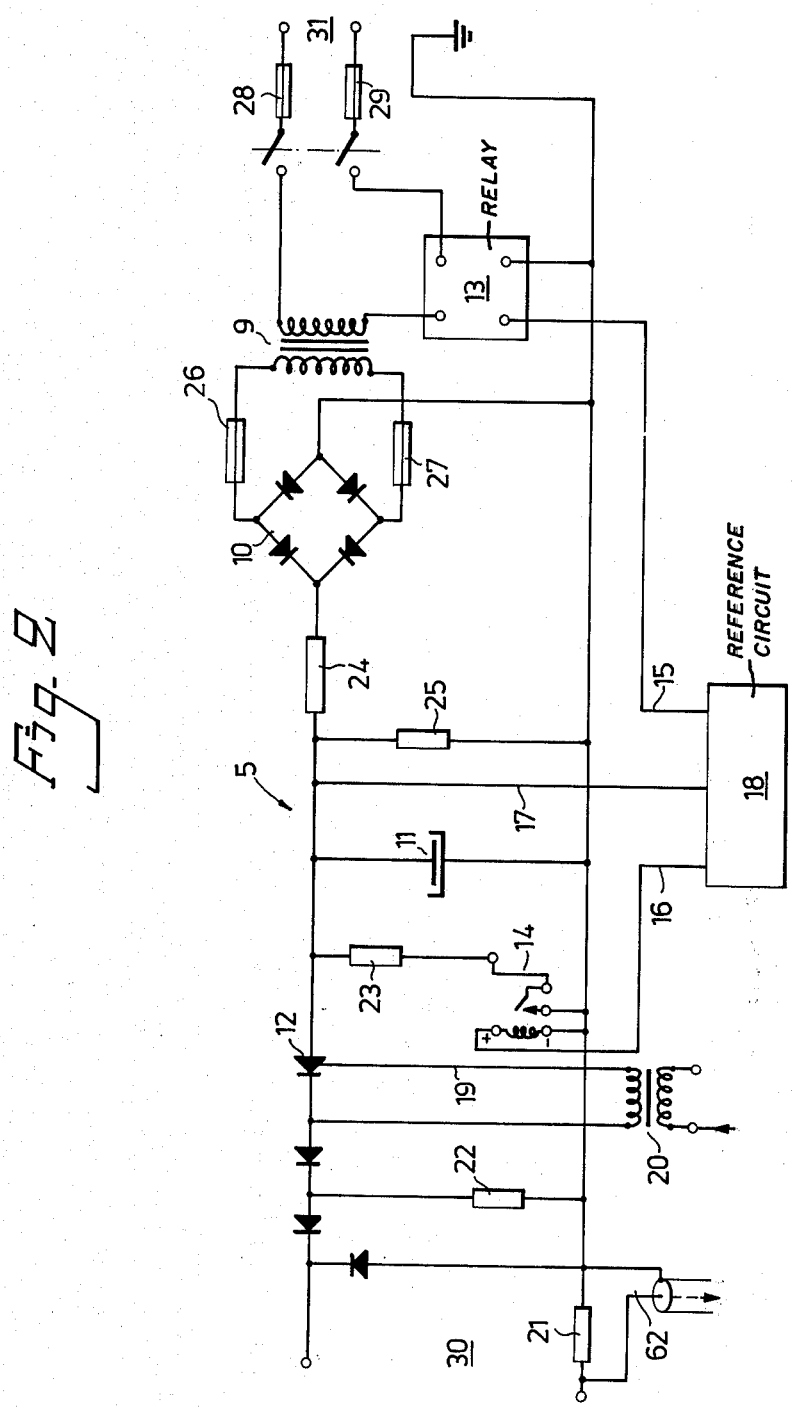
Figure 3:
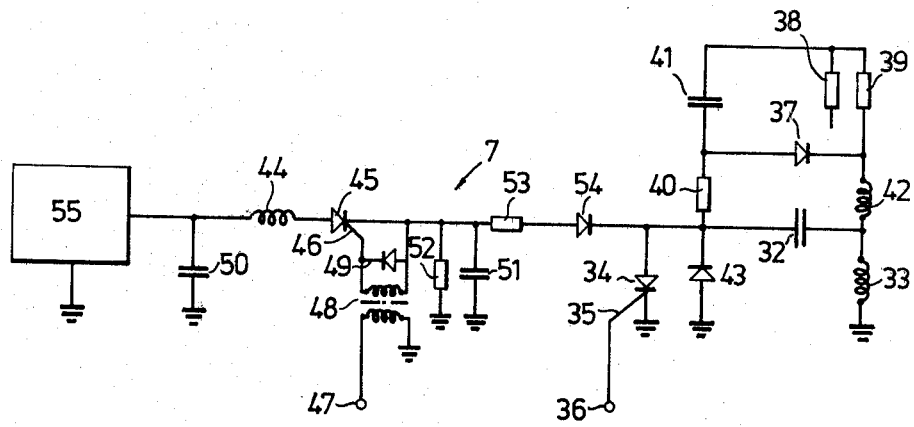
Figure 4:
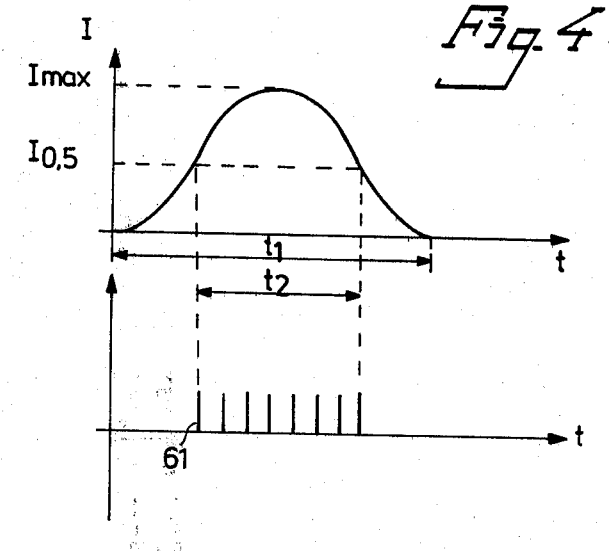

The invention is described in greater detail in the following, with reference to the accompanying drawings, in which FIG. 1 is a block diagram of an apparatus according to the invention, FIG. 2 is a schematic diagram of an embodiment of a pulse generator for an electromagnet shown by way of example, FIG. 3 is a schematic diagram of a preferred embodiment of a pulse generator for a transmitter coil, FIG. 4 is a curve of the magnetic field strength of the electromagnet and a series of ultrasonic pulses as a function of time.

In FIG. 1 a first electromagnet 1 is used for transmitting, and a second electromagnet 2 is used for receiving. Both magnets have associated windings 3 and, respectively, 4.

The magnet cores of the electromagnets 1,2 preferably are of ferromagnetic material and designed so that eddy currents therein are prevented. The magnet cores preferably are laminated, but cores of ferromagnetic power or threads may also be used.

The windings 3,4 of the electromagnets 1,2 are connected to a first pulse generator 5 capable to generate short, very strong pulses. The length of the pulses preferably is 0.5 to 100 ms.

A preferred embodiment of the pulse generator is shown in FIG. 2. The pulse generator is connected to and controlled by a programmed time circuit 6 of known suitable type.

The said time circuit also is capable of controlling a second pulse generator 7 shown in FIG. 3, which generator is capable of generating pulses of supersonic frequency to a transmitter coil 8. Said coil 8 is so located relative to said first electromagnet 1, that the coil 8 will be within the magnetic field from the first electromagnet 1.

According to a preferred embodiment of the transmitter coil 8, it is designed as an endless track, such as a runner track seen from above, the straight portions of which are located beneath the poles of the magnet core 1.

The first pulse generator 5 is exemplified in FIG. 2. It comprises a transformer 9, a diode rectifier 10, a capacitor 11 or capacitor circuit with great capacitive reactance, for example 10 mF, amd a thyristor 12. There are further provided two relays 13,14, from which conductors 15,16 together with a conductor 17 connected after the rectifier 10 are connected to a reference circuit 18 shown by way of a block. Said reference circuit 18 is capable of evaluating pulse length and charging of the capacitor 11 and consists of a suitable known circuit.

The control conductors 19 of said thyristor 12 is connected to said time circuit 6 via a transformer 20. There are further provided resistances 21–25 and fuses 26–29 of different strength. The output 30 is connected directly to the windings 3,4 of the electromagnets 1,2, and the input 31 is connected to a voltage source, preferably mains voltage.

The windings of the electromagnets are connected in parallel with each other to the first pulse generator. The windings instead may be connected in series.

The function of the circuit shown in FIG. 2 is as follows. While charging of the capacitor 11 with direct voltage from the rectifier 10, the thyristor 12 is blocked. After the charging a control pulse is emitted from the time circuit to the thyristor 12 via the conductor 19. The capacitor 11 thereby is discharged through the windings 3,4 of the electromagnets 1,2. Thereafter the capacitor 11 again is charged, followed by a new discharge, a.s.o.

The second pulse generator 7 shown in FIG. 3 comprises a capacitor 32 and an inductance 33, through which the capacitor 32 is discharged after a thyristor 34 has become conductive in that a control pulse has been applied to its control conductor 35 via a first trigger input 36. The inductance 33 is the transmitter coil 8.

A thyristor 37, resistances 38–40, a capacitor 41 and an inductance 42 form a circuit, which implies that at conductive state of the thyristor 37 the capacitor 32 rapidly is discharged, and that the pulse thereby generated through the inductance rapidly attenuates.

The capacitor 32 is charged via an inductance 44. The charging is started in that a thyristor 45 is made conductive in that a control pulse has been applied to its control conductor 46 via a second trigger input 47, which comprises a transformer 48 and a diode 49. The charging circuit further includes capacitors 50,51, resistances 52,53 and a diode 54. A voltage unit 55 is provided for the circuit.

The function of the second pulse generator 7 is in principle as follows. By applying a control pulse to the second trigger input 47, the capacitor 32 is charged through the inductance 44. When the capacitor 32 has been charged, and a control pulse is applied to the first trigger input 36, the thyristor 34 is made conductive, whereby the capacitor 32 is discharged through the inductance 33, whereafter the inductance in the coil 33 again charges the capacitor 32, but with inverted polarity. Thereafter the capacitor 32 is re-charged through the diode 43 to its original polarity, whereafter further re-chargings are prevented when the thyristor 34 has re-assumed its blocking capacity. The transmitter coil, thus, has been taken through by a complete cycle of current at supersonic frequency. In order to protect against forced through-ignition of the thyristor 34, a further circuit with the thyristor 37, the capacitor 41, the resistors 38,39,40 and the inductor 42 is provided, the object of which is to rapidly discharge the capacitor 32 immediately before it again obtains its maximum charge of original polarity according to the description above. In this way the current pulse in the coil 8 ends suddenly even if the thyristor 34 tends to ignite through.

The pulse generator 7, thus, generates a short pulse well-defined in length, preferably a complete cycle of a sinusoidally shaped pulse, whereafter this pulse is completely extinguished as appears from above. The second pulse generator, of course, can be modified to emit pulses consisting of a plurality of complete cycles.

The pulse length can be varied within wide limits, as also the time between two successive pulses. The pulse length of a pulse consisting of a complete cycle preferably is 5 $\mu$s, and the time between two successive pulses is 0.5 ms. The charging time is equal to $\pi\sqrt{LC}$, where L is the inductance at 44 and C the capacitance at 32. The charging time preferably is 200 $\mu$s.

The supersonic frequency here referred to is below 2 MHz, preferably 50 KHz to 500 kHz.

A receiver coil 56 is located beneath the second electromagnet 2 in the same way and preferably with the same configuration as the transmitter coil 8.

Current pulses in the transmitter coil 8 induce a similar varying current into the surface layer of a test material 57. When a magnetic field B exists in a conductor, and a current 1 simultaneously flows in the conductor (i.e. the test material), a force F, so-called Lorentz-force, is formed on the conductor equal to $F = 1 \times B$, where 1 has the dimension A/m$^2$ and B Tesla.

In the present case the force oscillates with supersonic frequency, whereby thus ultra-sound is introduced into the test material. When the ultra-sound after having been reflected arrives at the receiver 2,4,56, the ultrasonic waves, according to Faraday's induction law, generate a corresponding electromotoric force, which yields a varying signal in the receiver coil 56.

This received signal passes through a high-pass filter, in order to eliminate components with low frequency. Said filter is associated to an amplifier 58 where the signal is amplified, whereafter the result is processed and/or demonstrated in a unit 59, for example a data processing unit and/or an oscilloscope or the like.

Between the amplifier 58 and the unit 59 an integrator 60, a so-called gated integrator of known type, is provided to store a received signal digitally by dividing the reception cycle into a number of addressable time intervals and thereby to store digitally the signal amplitude occurring in each time interval. The integrator 60 further is capable to add to every signal received further signals received. The values summed up after a number of signals received can thereafter be read from the integrator 60.

The arrangement described above refers to two electromagnets 1,2. For certain applications, however, only one electromagnet can be used, at which the transmitter coil as well as the receiver coil are provided.

At known ultrasonic technique by electromagnetic ultra-sound the emitted pulses are of an undefined length, due to the formation of a tail after the pulse proper. The tail length generally is such as to actuate the receiver during the time the receiver is intended to receive reflections from the pulse proper. This implies a high noise level and/or interference level. In the case of testing non-magnetic material, the known technique implies such a high noise level and/or interference level that the signal proper hardly can be distinguished.

For many cases, however, it is insufficient to emit only one pulse with well-defined length, because interferences of different kind render it difficult to detect the ultrasonic echo signal with high safety. One example of such testing is the testing of steel above the Curie-temperature, i.e. when the steel is not magnetic. Furthermore, cooled electromagnets with associated cooling arrangements are relatively expensive.

According to the present invention, preferably a pulsed magnetic field from the electromagnets 1,2 is used, the duration of which is short relative to the time between the magnetic field pulses.

Due to the fact that the pulsed magnetic field has a short duration, for example 30 ms, at a pulse repetition of 5 per second, very strong magnetic fields can be formed without appreciably heating the electromagnets.

The electromagnets 1,2 according to the present invention are air-cooled. Compressed air from a suitable known compressed air unit (not shown) is caused to flow about the magnet core.

According to the present invention, a plurality of ultrasonic pulses are transmitted and received during the magnetic field generated by the electromagnets 1,2.

The programmed time circuit 6 is capable to emit a signal to the control conductor 19 of the thyristor 12 of the first pulse generator 5, whereby the capacitor 11 is discharged.

When the magnetic fields of the electromagnets 1,2 have obtained about half their maximum amplitude, the capacitor 32 is discharged in that the programmed time circuit 6 emits a control pulse to the first trigger input 36 of the second pulse generator 7. Thereby a sinusoidally-shaped signal is emitted by the transmitter coil 8, which signal is converted into a corresponding ultrasonic wave in the test material 57, which wave is reflected and received. The signal corresponding to the reflected ultrasonic wave in the receiver coil 56 is amplified and stored in the integrator 60. After a time sufficient for the ultrasonic wave to have been extinguished, during which time the capacitor 32 in the second pulse generator 7 again has been charged, a new signal of equal sinusoidally-shape is emitted by the transmitter coil 8. The resulting ultrasonic wave is reflected, received and stored in the same way in the integrator 60 where it is added, as mentioned, to the signal received first. This is repeated until the magnetic field of the electromagnets 1,2 has decreased to half its maximum strength.

For the said charging of the capacitor 32 the time circuit 6 is capable of emitting a control pulse on the second trigger input 47 of the second pulse generator 7.

The time circuit 6 further emits signals to the integrator 60 both when the fields of the electromagnets commence to be built up and when every ultrasonic pulse is emitted. The integrator 60 further receives a signal from the time circuit 6 informing that the integrator delivers the stored information to the unit 59.

The number of emitted ultrasonic pulses during a pulse of magnetic fields from the electromagnets 1,2, of course, can vary very substantially. One example is shown in FIG. 4, which shows two diagrams with the same time axis. The upper one shows the current 1 through the electromagnets 1,2, and the lower one shows the points of time when signals of supersonic frequency are emitted through the transmitter coil 8. In the example in FIG. 4 the length of the magnetic field pulse $t_1$ is 30 ms, the time $t_2$ during which the magnetic field has a strength of >50% of its maximum strength is equal to 15 ms. Each pulse 61 of supersonic frequency has a duration $t_3$ of 5 $\mu$s. In the example the time between every pulse 61 is about 2 ms.

The time $t_1$ may, for example, be $0.5 \text{ ms} \leq t_1 \leq 100 \text{ ms}$, the time $t_2 0.25 \text{ ms} \leq t_2 \leq 50$ ms, and the time $t_3$ may be $0.5 \text{ }\mu\text{s} \leq t_3 \leq 100 \text{ }\mu\text{s}$. $t_3$ always is substantially shorter than $t_2$.

After a series of pulses 61, in the example eight pulses, the integrator 60 contains the total of the amplitude for all pulses divided in time steps. This content is demonstrated or processed by the unit 59. The signal thus demonstrated corresponds to a series of ultrasonic wave reflexes of the same or similar appearance, but weaker than the stored signal. This implies, thus, that an interference occurring at a pulse 61 will give a proportionally smaller contribution to the total signal. This contribution is the smaller the more pulses are emitted in a series.

By the method and apparatus according to the invention, thus, a higher signal strength in relation to the noise level and other interferences is obtained. This implies that an ultrasonic wave reflection can be distinguished and processed much more distinctly than it has been possible with known technique.

When the magnetic field of the electromagnets 1,2 has decayed, the next magnetic field is built up, and a series of pulses 61 are emitted, a.s.o.

When the aforesaid times are applied, it is ensured that a pulse is fully completed before the receipt of a reflected ultrasonic wave takes place. It also is ensured that the ultrasonic wave is extinguished before the next emission takes place.

The time circuit 6 can be designed in known manner to emit said control pulses in a predetermined time order, or it can be designed to emit the control pulses to the first pulse generator in a predetermined time order and to emit the control pulses to the second pulse generator when the magnetic field or fields have obtained the intended strength. In the latter case the strength of the magnetic field can be read from a signal from an output 62 from the first pulse generator 5, see FIG. 2. The programmed time circuit 6 also may include a suitable data processing equipment, from which different sequences of pulses are controlled.

By the present invention, where a magnetic field is generated during a short time, during which a plurality of substantially shorter pulses of well-defined length of supersonic frequency are emitted, received and integrated, the signal/noise ratio is increased substantially.

The present invention, of course, can be modified without abandoning the invention idea. The structure of the pulse generators, for example, can be changed. One or more electromagnets can be used. The transmitter coil and the receiver coil can be the same, in which case a switch means is provided between the amplifier 58 and, respectively, the second pulse generator 7 and the coil for switching from transmission to receiving.

The invention, thus, must not be regarded restricted to the embodiment described above, but can be varied within the scope of the attached claims.

I claim:

1. A method of transmitting and receiving electromagnetically generated and received ultrasonic pulses, especially for non-destructive testing of electrically conductive material, particularly steel with a temperature above the Curie-temperature, comprising the steps of generating one or more magnetic fields by one or more electromagnets (1, 2, 3, 4) where said magnetic field is generated in the form of time-spaced pulses by a first pulse generator (5) and where each magnetic field pulse has a duration that is short as compared with the time interval between two successively occurring magnetic field pulses, characterized in that when the magnetic field or fields increase to at least a pre-selected strength, preferably 50 percent of maximum strength, a series of time-spaced electrical pulses of supersonic frequency are generated by a second pulse generator (7) and are supplied to a transmitter coil (8) within one of the magnetic fields to produce a corresponding number of ultrasonic pulses of well-defined length in said material, that a signal resulting from each ultrasonic pulse is received by a receiver coil (56) within one of said magnetic fields, that the receiver coil is scanned after each electrical pulse for sensing a received signal corresponding to each electrical pulse, that each such received signal is stored in an integrator (60) such that the series of received signals corresponding to said series of electrical pulses is summed up, whereafter the signal summed up in the integrator is emitted to a signal utilization unit (59), and that the last electrical pulse in said series is generated when said magnetic field or fields has decreased to a pre-selected strength, preferably 50 percent of maximum strength.

2. A method as defined in claim 1, characterized in that a first control pulse is supplied by a programmed timing circuit (6) to said first pulse generator (5) to generate said magnetic field or fields and thereafter a further series of pairs of second control pulses are supplied by said timing circuit to said second pulse generator (7) to generate said series of electrical pulses.

3. A method as defined in claim 2, characterized in that said time circuit (6) is caused to first emit a control pulse to a thyristor (45) in the second pulse generator (7), which thyristor is included in a circuit for charging a capacitor (32), and thereafter is caused to emit a control pulse to a second thyristor (34) in the second pulse generator (7) included in a circuit for discharging the capacitor (32), where such a pair of control pulses are caused to be emitted from the time circuit (6) for every pulse in the above series of pulses, and that said discharge takes place via an inductance (33) constituted by the transmitter coil (8).

4. A method as defined in claim 1, characterized in that each of the magnetic field pulses has a duration of 0.5 ms to 100 ms, preferably 30 ms, and that each of said electrical pulses has a duration of 0.5 µs to 100 µs, preferably 10 µs.

5. An apparatus for transmitting and receiving electromagnetically generated ultrasonic pulses, especially for non-destructive testing of electrically conductive material, comprising one or more electromagnets (1, 2, 3, 4) for generating one or more magnetic fields, and a transmitter coil (8) located within one of said magnetic fields, a receiver coil (58) located within one of said magnetic fields, a first pulse generator (5) for supplying energy to the electromagnet (1, 2, 3, 4) or -magnets in the form of first time-spaced pulses each having a duration which is short as compared with the time between two successively occurring ones of said first pulses, characterized in that a second pulse generator (7) is connected to supply energy to said transmitter coil in the form of a series of second time-spaced pulses of supersonic frequency during the time period when the magnetic field or fields have obtained at least a preselected strength, preferably 50 percent of maximum strength, and continuing until the magnetic field or fields have decreased to corresponding preselected strength, that said transmitter coil is energized by said second pulses to produce a corresponding number of ultrasonic pulses of well-defined length in said material, that said receiver coil is positioned to receive a signal in response to each ultrasonic pulse which is produced in said material, and that scanning means (58, 60) are provided to scan the receiver coil (56) for a received signal corresponding to each of the ultrasonic pulses, which scanning means comprises an integrator (60) for digitally storing the received signals corresponding to said series of second pulses and for summing the signals thus received, and after every such series of second pulses to emit a summed up signal to a signal utilization unit (59).

6. An apparatus as defined in claim 5, characterized in that a programmed timing circuit (6) is provided and supplies a first control pulse to said first pulse generator (5) for causing said first generator to deliver energy to the electromagnet (1, 2, 3, 4) or -magnets, and thereafter supplies a series of pairs of additional control pulses to said second pulse generator (7) to cause said second generator to generate said series of pulses of supersonic frequency.

7. An apparatus as defined in claim 6, characterized in that the second pulse generator (7) comprises a charging circuit for a first capacitor (32) including an inductance (44) and a first thyristor (45), and a discharging circuit for the capacitor (32) including an inductance (33), which consists of the transmitter coil (8), a second thyristor (34) and a diode (43), where said first thyristor (45) in the charging circuit is connected to conduct when the first control pulse in each pair of control pulses is received from the timing circuit (6), whereby the capacitor (32) is discharged, and said second thyristor (34) in the discharging circuit is connected to conduct when the second control pulse in said pair is received from the timing circuit (6), and that the capacitor (32) during half a cycle is discharged via the second thyristor (34) and during the subsequent half of a cycle is discharged via the diode (43).

8. An apparatus as defined in claim 5 wherein two electromagnets (1, 2) are provided, the windings (3, 4) of which are connected in parallel or in series to the first pulse generator (5), and that the transmitter coil (8) is located at one electromagnet (1), and the receiver coil (56) is located at the other electromagnet (2).

9. An apparatus as defined in claim 7, characterized in that the second pulse generator (7) further comprises a rapid discharge circuit having a third thyristor (37), a second capacitor (41), resistors 38, 39, 40 and inductor (42), said rapid discharge circuit being connected to rapidly discharge said first capacitor (32) at a predetermined moment, preferably immediately before the first capacitor (32) again obtains its maximum charge of the original sign after having been discharged through the second thyristor (34) and then through the diode (43), whereby the current in the transmitter coil (8) ceases abruptly, irrespective of the tendency of the second thyristor (34) to ignite through.

10. An apparatus for non-destructively testing electrically conductive non-magnetic material, such as steel at a temperature above the Curie temperature, with ultrasound, comprising means for producing a pulse of one or more magnetic fields in the region of said material, a transmitter coil located within one of said fields, means for supplying a series of time-spaced electrical pulses to said transmitter coil only during a preselected time period in which the field strength of said magnetic field pulse is not less than a preselected value, said time period being shorter than the duration of said magnetic field pulse, said transmitter coil being energized by said electrical pulses to produce a corresponding number of ultrasonic sound pulses in said material, a receiver coil within one of said fields for receiving a signal in response to each of said ultrasonic pulses to provide a series of such signals, and means electrically connected to said receiver coil and including means for integrating the signals in said series of such signals to provide a summation of the signals in said series of such signal, and means for utilizing said summation of signals.

11. A method of non-destructively testing a non-magnetic, electrically conductive material, such as steel at a temperature above the Curie temperature, with ultrasound, comprising the steps of producing a pulse of a magnetic field in the region of said material, energizing a transmitter coil within said field with a series of time-spaced electrical pulses to produce a corresponding series of ultrasonic sound pulses in material, said series of electrical pulses being supplied to said transmitter coil only during a pre-selected time period in which the field strength of the magnetic field pulse is not less than a preselected value, and said time period being shorter than the duration of the magnetic field pulse, receiving a signal in response to the production of each of said ultrasonic pulses to provide a series of received signals, integrating the signals in said series of received signals to provide a further signal which is a function of the summation of signals in said series of received signals, and utilizing said further signal to determine the presence or absence of a defect in said material.

12. The method defined in claim 11 wherein said preselected value of the strength of said magnetic field pulse is approximately 50 percent of the maximum strength of the magnetic field pulse.

* * * * *